(12) United States Patent
Witte

(10) Patent No.: US 6,421,567 B1
(45) Date of Patent: Jul. 16, 2002

(54) IMPLANTABLE LEAD WITH MECHANICAL AND ELECTRICAL SELECTIVELY OPERABLE ELECTRODES

(75) Inventor: Joachim Witte, Berlin (DE)

(73) Assignee: Biotronik Mess-und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/603,077

(22) Filed: Jun. 26, 2000

(30) Foreign Application Priority Data

Jun. 25, 1999 (DE) .......................................... 199 30 271

(51) Int. Cl.⁷ ............................................... A61M 1/05
(52) U.S. Cl. ........................ 607/122; 607/119; 607/123
(58) Field of Search .................... 607/116, 119, 607/122–123; 439/909

(56) References Cited

U.S. PATENT DOCUMENTS

| | | | |
|---|---|---|---|
| 4,628,934 A | * | 12/1986 | Pohndorf et al. ............. 607/27 |
| 4,848,352 A | | 7/1989 | Pohndorf et al. |
| 5,423,873 A | * | 6/1995 | Neubauer et al. ............. 607/68 |
| 5,480,421 A | * | 1/1996 | Otten .......................... 607/122 |
| 5,968,086 A | * | 10/1999 | Bonner et al. .............. 607/122 |

* cited by examiner

*Primary Examiner*—Kennedy Schaetzle
*Assistant Examiner*—Kristen Droesch
(74) *Attorney, Agent, or Firm*—Venable; Robert Kinberg; Catherine M. Voorhees

(57) ABSTRACT

An implantable electrode arrangement which includes an electrode line (10, 10') with a plurality of electrically conductive surface regions (14, 16) in the region of the distal end of the electrode line for outputting electrical signals to a heart and/or for receiving signals from a heart, which can be electrically connected by way of the electrode line (10, 10') to a cardioelectric device such as a defibrillator or cardiac pacemaker, which device receives electrical signals and/or outputs pulses, wherein there are switching means (20, 22; 34) which are of such an arrangement and configuration that the connection between individual ones of the electrically conducting surface regions (14, 16) and the cardioelectric device can be permanently switched on or off in the region of the electrode line (10, 10').

17 Claims, 4 Drawing Sheets

IMPLANTABLE LEAD WITH MECHANICAL AND ELECTRICAL SELECTIVELY OPERABLE ELECTRODES

BACKGROUND OF THE INVENTION

The invention concerns an implantable electrode arrangement which includes an electrode lead with a plurality of electrically conducting surface regions in the region of the distal end for outputting electrical signals to a heart and/or for receiving signals from a heart. The output and/or received signals can be electrically connected by way of the electrode lead to a cardioelectric device for a defibrillator or cardiac pacemaker where the cardioelectric device receives electrical signals and/or outputs pulses.

Electrode arrangements with an electrode line and a plurality of electrically conducting surface regions, for example of tip or ring electrodes, at a distal end of the electrode line are known for example from EP 0 571 797, U.S. Pat. No. 4,848,352 and U.S. Pat. No 4,628,934. In known electrode arrangements, the electrically conducting surface portions which serve as stimulation or sensing electrodes are individually connected to a cardiac pacemaker or defibrillator by means of electric lines which extend in the electrode lead. Each of the above-mentioned publications also describes selecting from the plurality of electrodes or electrode combinations, the respectively most suitable ones thereof in order to use them for example for stimulation of a human heart. A disadvantage with the known electrode arrangements is that they can usually only be employed together with specifically adapted cardiac pacemakers or defibrillators which make it possible at the proximal end of the electrode lead or line to contact all feed lines which lead to the electrically conducting surface regions.

Conventional electrode arrangements are those in which only one or two electrical conductors extend in the electrode line, depending on whether the electrode arrangement is intended for unipolar or bipolar stimulation.

Electrode lines with a single-wire connection between the proximal end of the electrode line and the electrically conducting surface regions at the distal end of the electrode line are suitable for unipolar stimulation in which stimulation pulses are outputted between the electrically conducting surface regions at the distal end of the electrode line and a neutral electrode such as for example a casing of a cardiac pacemaker. Also known moreover is bipolar stimulation in which the stimulation energy is outputted between various ones of the electrically conducting surface regions at the distal end of the electrode line. For bipolar stimulation, the electrode line has a two-wire connection between the proximal and distal ends, such connection being made by way of two separate electric lines.

SUMMARY OF THE INVENTION

The object of the invention is to also make available the advantages of electrode arrangements having a plurality of electrically conducting and individually operable surface regions, for cardiac pacemakers or defibrillators having conventional one-wire or two-wire connections.

According to the invention, that object is attained by an electrode arrangement of the kind set forth in the opening part of this specification, which is distinguished by switching means that are of such an arrangement and configuration that the connection between individual ones of the electrically conducting surface regions and the cardioelectric devices can be permanently switched on or off in the region of the electrode lead. Such an electrode arrangement makes it possible for firstly any of the electrically conducting surface regions to be selected by virtue of receiving or outputting electrical signals and then used permanently by way of a conventional one-wire or two-wire line in the electrode lead with the cardioelectric device such as a defibrillator or cardiac pacemaker.

For that purpose it is advantageous if the switching means are of such a configuration that they retain their switching state in the current-less condition.

In a preferred embodiment, the switching means are electrically actuable by way of the electrode lead. For that purpose, the electrode lead preferably has a decoder which is connected on the one hand to the switching means and on the other hand to at least one electric line—for example the usual one-wire or two-wire line which connects the electrically conducting surface regions to the cardiac pacemaker. The decoder is of such a nature that it can receive control signals by way of the electric line and can individually actuate the switching means in dependence on the control signals. In the minimum situation, an electrode arrangement of that kind needs only one single electrical conductor which goes from the proximal end of the electrode lead to the switching means, the decoder and the electrically conducting surface regions at the distal end of the electrode lead. The reference potential for the control signals can then be afforded, for example, by way of a neutral electrode with the casing of the pacemaker. After the most suitable electrodes or electrode combinations have been ascertained, then by means of the decoder and the switching means they can be permanently connected to, for example, a cardiac pacemaker by way of the one electric line in the electrode lead. The cardiac pacemaker can be a conventional cardiac pacemaker which then also enjoys the advantages of the individually ascertained, most suitable electrode configurations.

For the permanent connection of the electrically conducting surface regions to the electrical conductor in the electrode lead or conversely for permanently separating individual surface regions from the electrical conductor, it is possible to use electric components which for switching or breaking the connection require a higher level of electrical power than can be made available for example by way of the one-wire conductor and the neutral electrode as the counterpart electrode. In order to be able to use such electric components, the electrode arrangement includes preferably an energy storage means which is connected to the switching means and/or the decoder and which can be charged up by way of the electrode lead with a lower level of power than it can output by way of the switching means and/or the decoder. Preferably, the energy storage means is an electrical capacitor which is charged with a high level of resistance, for example, by way of a fine-wire line and the neutral electrode and can quickly output the electrical energy accumulated in that way for switching the switching means. This can be achieved, for example, by switching through a power field transistor or burning through a thyristor. In that way a switching connection is permanently made or permanently broken. The last-mentioned case is the preferred one, in which the switching elements are such that, for switching off a connection between the electrode lead and an electrically conducting surface region, the connection can be permanently destroyed. The energy storage means is preferably adapted to output the energy required for that purpose.

Even if the electrical energy storage means, in particular in relation to such electrodes with a single-wire connection between the proximal and the distal ends, because of the level of power which is to be kept down for charging the capacitor, enjoys particular advantages so that affected heart tissue is not already stimulated upon charging of the energy storage means, such an energy storage means can equally advantageously be used in relation to an electrode lead with a two-wire connection between the proximal and the distal ends, with which, due to the principle involved, higher levels of power can be transmitted to the energy storage means, than in the case of an electrode lead with only a one-wire connection.

Particularly for checking out individual surface regions or combinations, a preferred electrode arrangement is one which includes control means which at the input side can be connected to the cardioelectric device by way of at least one electric line for signals to or from the electrically conducting surface regions and which at the output side are connected to the electrically conducting surface regions which are such that they are controllable by control signals received by way of the electric line, in such a way that individual surface regions or combinations of surface regions can be connected to the cardioelectric device for outputting and receiving signals for ascertaining the permanent connection to the electrically conducting surface regions which are suitable for the cardioelectric device. The last-mentioned variant therefore does not concern permanent connection of the electrically conducting surface regions to the cardioelectric device, but a testing connection of the surface regions to the device prior to permanent setting of a suitable electrode combination.

An alternatively preferred electrode arrangement is distinguished by a rod or bar which is guided longitudinally movably or rotatably relative to the electrode line and which has actuating elements for mechanical switching elements, with which the connection between individual ones of the electrically conducting surface regions and the cardioelectric device can be permanently switched on or off in the region of the electrode lead. By means of such a bar and the switching elements, the switching elements can be so displaced or rotated in the electrode lead that they selectively make or break a contact between individual ones of or a plurality of the electrically conducting surface regions and an electric line in the electrode lead. As the corresponding mechanical switching elements do not change over without being actuated by the bar, in that way a connection is permanently made or interrupted between the electrically conducting surface regions and the electric conductor in the electrode lead.

In connection with the last-mentioned alternative embodiment, a preferred electrode arrangement is one in which the switching elements are arranged longitudinally movably or rotatably in the region of the distal end of the electrode lead and are in electrical contact with at least one electric line in the electrode lead, and also have contact regions which, in one of at least two possible positions of the switching elements, contact a counterpart contact which is connected to at least one electrically conducting surface region, and further have switching cams or projections with which a switching element is movable by means of corresponding counterpart cams or projections on the bar, by means of the bar, in such a way that the switching means are movable by means of the bar into a respective position of connecting a surface region to the cardioelectric device and a position of separating a surface region from the cardioelectric device. The principle of two cams or projections which are to be brought into engagement with each other in order to rotate and longitudinally slide a mechanical element is known to the man skilled in the art in all its various forms and can be easily transferred to a bar with a plurality of actuating cams or projections in which the actuating cams or projections are so displaced relative to each other that all mechanical switching elements can be displaced or rotated by a bar individually and independently of each other.

In accordance with the invention the above-specified object is also achieved by means of a method of operating the described electrode arrangement, in which firstly surface regions which are suitable for signal reception and/or stimulation are ascertained and then the appropriate surface regions are permanently connected to at least one electric line of the electrode line while the other surface regions are permanently separated from the electric line. The method is therefore a two-stage method, firstly provisional connections are made between the electrically conducting surface regions and for example a cardiac pacemaker in order to test the electrically conducting surface regions or combinations in terms of their suitability. The above-mentioned control means serve for that purpose. Then, the most suitable surface regions are permanently connected to an electric line leading to the proximal end of the electrode line or accordingly all surface regions apart from the most suitable surface regions are permanently separated from the electric line.

BRIEF DESCRIPTION OF THE DRAWINGS

The invention will now be described in greater detail by means of embodiments with reference to the accompanying drawings in which:

FIGS. 3a and 3b show a view in longitudinal section through a part of the electrode lead illustrated in FIG. 1, in an alternative variant.

DETAILED DESCRIPTION OF THE DRAWINGS

Figure 1:
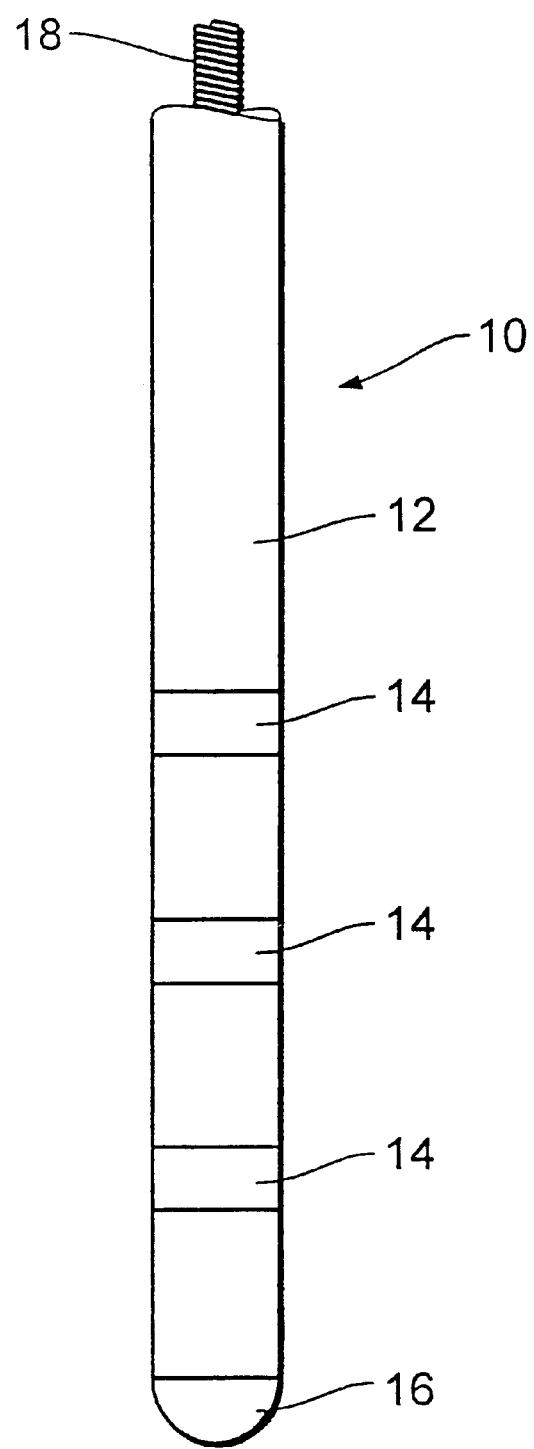
FIG. 1 shows the distal end of an electrode lead with electrically conducting surface regions as electrodes.

The distal end shown in FIG. 1 includes an electrode lead 10 with an insulating case 12 and ring electrodes 14 disposed therein as well as a tip electrode 16 at the outermost end of the electrode lead 10 and serves for the transmission of electrical signals from and to the electrodes 14 and 16. The electrodes 14 and 16 can include, for example, metal. The essential consideration is that the electrodes 14 and 16 represent electrically conducting surface regions of the electrodes lead 10, which can be at least partly connected to the electric line 18. The structure of the electrode lead 10 can be seen from the view in the longitudinal section of FIG. 2, through the electrode lead 10 in the region of two ring electrodes 14. Shown therein is the coiled electric line 18 which extends within the insulating case 12. The following electrical components are disposed between the line 18 and each ring electrode 14: in each case, a field effect transistor 20, a decoder or a control unit 22, and a capacitor 24. The field effect transistors 20 are power transistors of low forward resistance in the conducting state. They each represent a respective switching means for making or breaking an electrical connection between the line 18 and a respective ring electrode 14. The field effect transistors 20 are actuated by the control unit or decoder 22. The control unit or decoder 22 have two control inputs of which one is connected to the electric line 18 and the other to a respective ring electrode 14. By way of the control inputs, the control unit 22 can receive control signals which are outputted for example by a cardiac pacemaker by way of the electric line 18 and a neutral electrode, such as the cardiac pacemaker casing, and which accordingly are represented as a potential sequence which is between the line 18 and a ring electrode 14. In this case, the ring electrode 14 is connected to the neutral electrode by way of a body into which it is inserted.

The energy supply for the control unit 22 is afforded by a capacitor 24 which is also arranged between the line 18 and a respective ring electrode 14. The capacitor 24 is supplied with energy by way of the electric line on the one hand and on the other hand by way of the ring electrode 14 and the neutral electrode (not shown) corresponding thereto, from the cardiac pacemaker, and charged with a high level of ohmic resistance.

By way of suitable control signals, any one of the electrodes 14 and 16 can be connected to or disconnected from the line 18 by means of the control units 22 and the field effect transistors 20.

Figure 2:
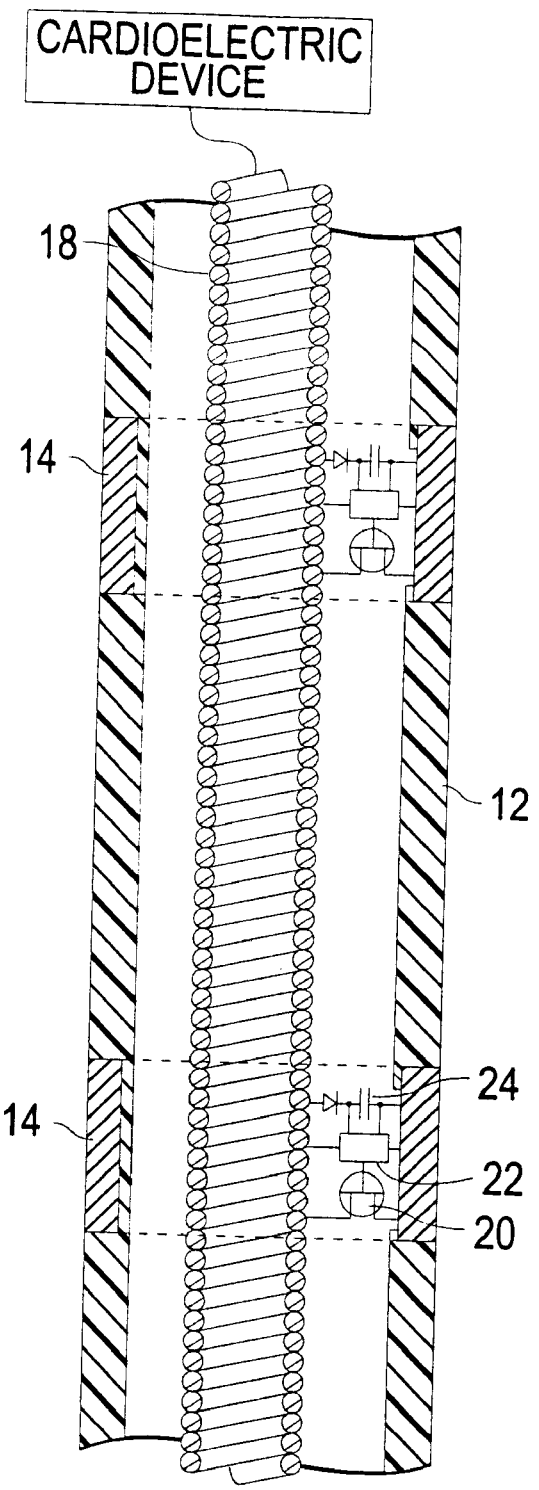
FIG. 2 is a view in a longitudinal section through a part of the electrode lead shown in FIG. 1.

Instead of the control and switching means shown in FIG. 2, it is also possible to use for example EEPROMs, that is to say electrically erasable and programmable read only memories which are configured by way of suitable control signals and which provide for the desired connections to the electrodes 14 and 16 and the line 18.

As an alternative, it is also possible to provide simple wire connections between electrodes 14 and 16 and line 18, which if necessary are burnt through by suitable control means by virtue of electrical energy stored in a capacitor, in order to permanently interrupt a connection between an electrode 14 or 16 and line 18.

Figure 3B:
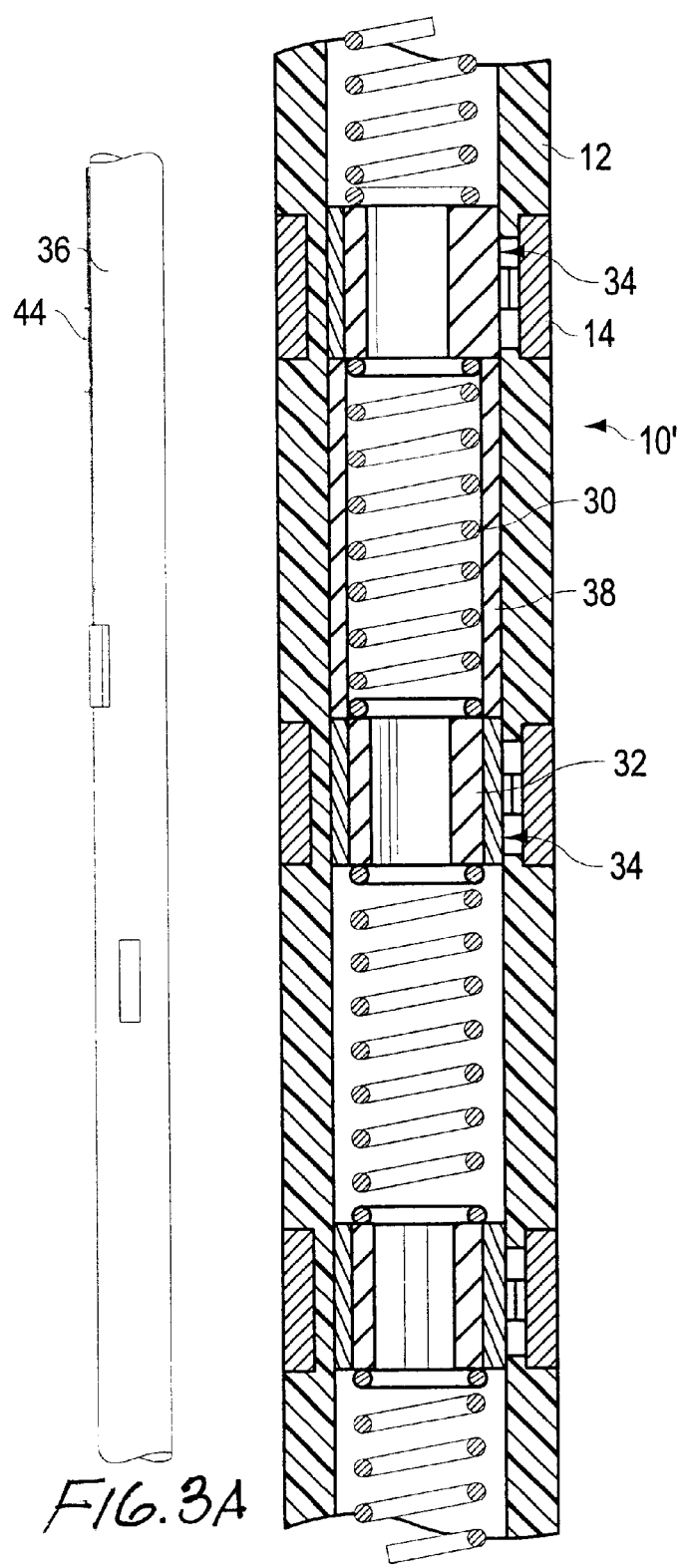
Figure 4:
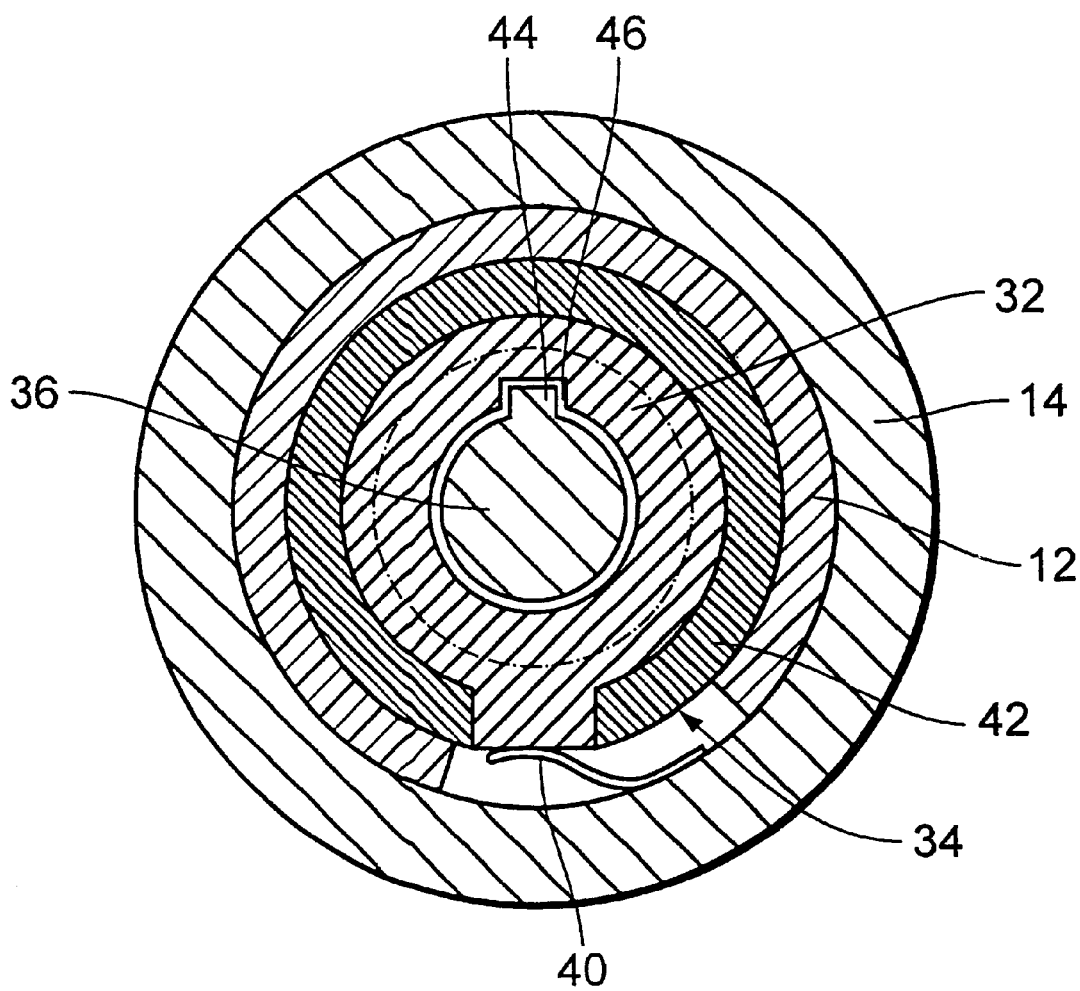
FIG. 4 is a view in cross-section through the variant in FIG. 3 in the region of a ring electrode.

As an alternative to the described electrical variants for permanently making or breaking an electrical connection between the electrodes 14 and 16 at the line 18, there is also provided the mechanical variant which is illustrated in FIGS. 3a and 3b and FIG. 4. As the view in section through the electrode lead 10 in FIG. 3b shows, the external structure of the electrode lead 10 is identical to the variants described hereinbefore: ring electrodes 14 in the form of metal rings are disposed onto an insulating case 12. The electric line is not in the form of a continuous wire coil in the region of the illustrated distal end of the electrode line, but is formed in a portion-wise manner by compression springs 30 and a respective metal body 32 of mechanical switching elements 34.

For the sake of improved understanding FIGS. 3a and 3b, it is to be noted that for the sake of enhanced clarity of the drawing these Figures show the electrode lead 10 in a partially dismantled condition. In the assembled condition, the bar 36 which is shown in FIG. 3a extends in coaxial relationship with the electrode lead 10' and within the same thus passing through switching elements 34 and extending within compression springs 30.

As can be seen from FIG. 3b, the switching elements 34 are fixed in their respective axial positions in the electrode line 10' by spacer sleeves 38 in such a way that the switching elements 34 are disposed in opposite relationship to the ring electrodes 14 on the inside thereof. The switching elements 34 are arranged rotatably about the longitudinal axis of the electrode lead 10'. A respective switching contact 40 of the ring electrodes 14 contacts the output surface of each of the switching elements 34.

As can be seen in particular from FIG. 4 showing a view in cross-section through the electrode lead 10' in the region of a the upper ring electrode 14 and switching element 34 shown in FIG. 3b, the switching or rubbing contact 40 can make an electrical contact between the metal body 32 of the switching element 34 and the ring electrode 14 when the switching element 34 is in an angular position which is suitable for that purpose. In positions other than the angular position of the switching element 34, that is shown in FIG. 4, insulation 42 on the outside surface of the switching element 34 prevents electrical contact from occurring between the metal body 32 of the switching element 34 and the ring electrode 14. In that fashion, when the switching element 34 is in the position shown in FIG. 4, an electrical connection is made between the electric line in the electrode lead 10' and the ring electrode 14, by way of the compression springs 30 and the metal body 32 of the switching elements 34 and the rubbing contact 40. If the switching element 34 is in an angular position different from that illustrated, the electrical connection between the electric line and the electrode 14 is broken.

For selecting the angle and thus, the switching positions of the switching element 34, the arrangement has the rod or bar 36 which for that purpose is mounted rotatably and longitudinally slidably in the electrode lead 10'. The bar 36 has switching cams or projections 44 which can each be brought into engagement in a respective groove 46 in the metal body 32 of the switching element 34. That is effected by longitudinal sliding movement of the bar 36. The spacing of the switching cams 44 in the longitudinal direction of the bar 36 is so selected that only one respective switching cam engages into a groove 46 in a switching element 34. Switching element 34 into which a switching cam 44 of the bar 36 engages can be moved into an angular position by rotation of the bar 36 about its longitudinal axis and thus into an angular position which makes or breaks the final connection in relation to the respective ring electrode 14.

What is claimed is:

1. An implantable electrode arrangement comprising:
    an insulating case having a distal end and a plurality of electrically conductive surface regions spaced from one another in a line at the distal end;
    an electric line extending through the insulating case to the distal end, said electric line enabling connection of the plurality of electrically conductive surface regions to a cardioelectric device, said plurality of electrically conductive surface regions capable of at least one of outputting electrical signals to a heart and receiving electrical signals from a heart; and
    a plurality of switching means, arranged at the distal end of the insulating case, for electrically connecting a respective electrically conductive surface region to the electric line wherein a permanent switching of the switching means selectively provides permanent connection and permanent disconnection between respective electrically conductive surface regions and the electric line.

2. The implantable electrode arrangement according to claim 1, wherein the permanent switching depends upon the at least one of outputting electrical signals to a heart and receiving electrical signals from a heart of a respective conductive surface region, and wherein conductive surface regions that are suitable for at least one of signal reception from the heart and stimulation of the heart are permanently coupled to the electric line, while remaining conductive surface regions are permanently separated from the electric line.

3. The implantable electrode arrangement according to claim 1, further comprising control means, arranged in the insulating case and coupled to the electric line and to each electrically conductive surface region, for receiving control signals from at least one of the electric line and a respective electrically conductive surface region, said control means capable of being coupled to the cardioelectric device via the electric line and being electrically coupled to said switching means wherein at least one of individual conductive surface regions and combinations of conductive surface regions are coupled to the cardioelectric device for outputting and receiving signals to ascertain which electrically conductive surface regions are suitable for permanent connection to the cardioelectric device.

4. The implantable electrode arrangement according to claim 1, wherein the switching means are such that the connection between conductive surface regions and the electric line can be permanently destroyed.

5. The implantable electrode arrangement according to claim 4, wherein the energy storage means is adapted to output the energy required for destruction of the connection between respective electrically conductive surface regions and the electric line.

6. The implantable electrode arrangement according to claim 1, wherein the switching means have an ON state and an OFF state, the state of the switching means being retained in a current-less condition.

7. The implantable electrode arrangement according to claim 6, wherein the switching means are actuated via the electric line.

8. The implantable electrode arrangement according to claim 1, wherein the switching means are actuated via the electric line.

9. The implantable electrode arrangement according to claim 8, further comprising a plurality of decoders, each decoder having two control inputs, one control input being coupled to the electric line and the second control input being coupled to a respective conductive surface region, wherein a respective switching means is coupled to at least a respective one of the plurality of decoders in order to receive control signals to individually actuate the respective switching means in dependence on the control signals.

10. The implantable electrode arrangement according to claim 9, wherein the electric line is a feed line for at least one of electric signals to one of the electrically conductive surface regions and electrical signals from one of the electrically conductive surface regions.

11. The implantable electrode arrangement according to claim 9, further comprising a plurality of energy storage means for storing and supplying energy, each respective energy storage means being coupled to at least one of the respective switching means and the respective decoder and being charged up via the electric line with a lower level of power than the respective energy storage means outputs to at least one of the respective switching means and the respective decoder.

12. The implantable electrode arrangement according to claim 11, wherein the energy storage means is adapted to output the energy required for destruction of the connection between respective electrically conductive surface regions and the electric line.

13. The implantable electrode arrangement according to claim 11, wherein the energy storage means is an electrical capacitor.

14. The implantable electrode arrangement according to claim 13, wherein the energy storage means is adapted to output the energy required for destruction of the connection between respective electrically conductive surface regions and the electric line.

15. A method of operating an electrode arrangement according to claim 1, comprising the steps of:
   ascertaining which of the plurality of electrically conductive surface regions are suitable for at least one of signal reception from the heart and stimulation of the heart; and
   then, permanently connecting to the electric line the ascertained conductive surface regions, and permanently separating the remaining conductive surface regions from the electric line.

16. An implantable electrode arrangement comprising:
   an insulating case having a distal end and a plurality of electrically conductive surface regions spaced from one another in a line at the distal end;
   an electric line extending through the insulating case to the distal end, said electric line enabling connection of the plurality of electrically conductive surface regions to a cardioelectric device, said plurality of electrically conductive surface regions capable of at least one of outputting electrical signals to a heart and receiving electrical signals from a heart; and
   a plurality of switching means, arranged at the distal end of the insulating case, for electrically connecting a respective electrically conductive surface region to the electric line wherein a permanent switching of the switching means selectively provides permanent connection and permanent disconnection between respective electrically conductive surface regions and the electric line; and
   a bar, which is at least one of longitudinally moveable and rotatable relative to the electric line, said bar having a plurality of actuating elements disposed thereon, wherein said switching means include mechanical switching elements that correspond to respective electrically conductive surface regions and when said bar is inserted into said insulating case, the mechanical switching elements can permanently connect the electric line with individual ones of the electrically conductive surface regions if the actuating element is in the ON position, and if the actuating element is in the OFF position, the mechanical switching elements permanently disconnect the electrically conductive surface regions from the electric line.

17. The implantable electrode arrangement according to claim 16, wherein the switching elements are arranged at least one of longitudinally moveable and rotatable in the distal end of the insulating case, are in electrical contact with the electric line, and have contact regions which in one of at least two possible positions of the switching elements contact a counterpart contact coupled to a respective electrically conductive surface region, said switching elements having a groove for receiving a switching cam disposed on said bar that serves as the actuating element and being movable by means of said at least one of longitudinally moveable and rotatable bar into the ON position to connect a conductive surface region to the cardioelectric device and into the OFF position to separate a conductive surfaced region from the cardioelectric device.

* * * * *